United States Patent [19]

Norris et al.

[11] Patent Number: 5,317,150
[45] Date of Patent: May 31, 1994

[54] POLARIMETER CALIBRATION METHOD AND APPARATUS

[75] Inventors: Harry Norris; Jennifer L. Horn, both of Huntingdon, United Kingdom

[73] Assignee: Optical Activity Limited, Ramsey, United Kingdom

[21] Appl. No.: 959,138

[22] Filed: Oct. 9, 1992

[30] Foreign Application Priority Data

Oct. 11, 1991 [GB] United Kingdom ............... 9121658

[51] Int. Cl.$^5$ ............................................. G01N 21/21
[52] U.S. Cl. ............................... 250/252.1; 250/341; 250/343; 356/367
[58] Field of Search .................. 250/338.1, 252.1 A, 250/339, 341, 343; 356/367, 368

[56] References Cited

U.S. PATENT DOCUMENTS 4,467,204 8/1984 Kysilka et al. ................. 250/343

FOREIGN PATENT DOCUMENTS 9213263 8/1992 PCT Int'l Appl. ............... 356/368

OTHER PUBLICATIONS

Galanov et al., "Infrared Polarimeters and Questions Relating to Contactless Measurement of Free-Carrier Concentrations in Semiconductors", Ind. Lab. (USA), 42(10), Oct. 1976, pp. 1530–1533.

Primary Examiner—Carolyn E. Fields
Attorney, Agent, or Firm—Lackenbach, Siegel, Marzullo & Aronson

[57] ABSTRACT

A method of calibrating polarimeter to work at an unknown wavelength comprising calibrating the polarimeter at a standard wavelength, using the calibrated polarimeter to measure a sample, measuring the same sample at the unknown wavelength and setting the polarimeter to give the same measurement at the said unknown wavelength as at the known wavelength. The method is particularly applicable to be calibration of a saccharimeter to work at an unknown wavelength in the near infra-red for the measurement of dark sugar samples. The invention is also a polarimeter or saccharimeter for carrying out the method.

7 Claims, 1 Drawing Sheet

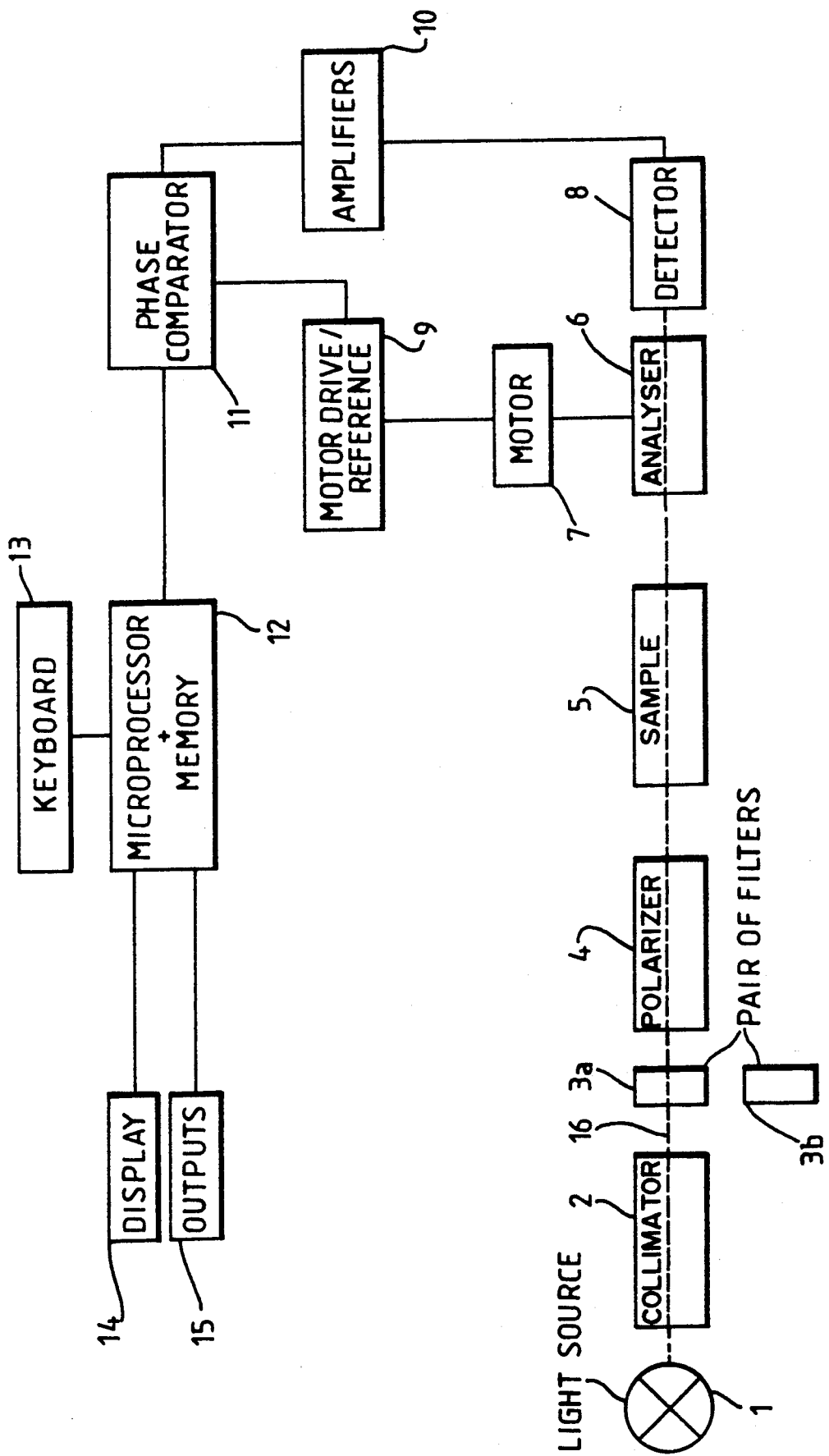

POLARIMETER CALIBRATION METHOD AND APPARATUS

FIELD OF THE INVENTION

The invention relates to polarimeters particularly, but not exclusively, of the kind comprising a polariser and an analyser one of which has a fixed orientation and the other of which is rotatable about its axis.

DESCRIPTION OF THE PRIOR ART

In such a polarimeter the polariser or analyser is rotated at constant speed about its axis and the resulting modulation of the light intensity is detected by a light detector arranged to detect the intensity of light transmitted by the analyser. The electrical output signal of the light detector in these circumstances is a $Sin^2$ waveform of two cycles per revolution of the analyser relative to the polariser. When a sample, the optical activity of which is to be measured, is placed between the polariser and the analyser, the phase of the output signal of the light detector is shifted in relation to the angular position of the polariser or analyser by an amount which is proportional to the optical rotation introduced by the sample. Measurement of this phase-shift in the output signal of the detector thus gives a measurement of the optical activity of the sample.

Such polarimeters are known from GB-B-1570067 and GB-B-1570068 (equivalent to U.S. Pat. No. 4,118,125).

SUMMARY OF THE INVENTION

The present invention is more particularly, but not exclusively, concerned with a saccharimeter, that is to say, a polarimeter calibrated to the International Sugar Scale. It is a disadvantage that at the wavelengths conventionally employed in saccharimeters, i.e. sodium yellow, mercury green, and helium-neon laser wavelengths, they are unable to penetrate, and are thus unable to measure, dark sugar samples. It would therefore be desirable to employ lower frequency wavelengths i.e. wavelengths in the near infra-red e.g. at around 880 nm since such frequencies will penetrate dark samples. It might also be desirable in some circumstances, e.g. in the drugs industry, to be able to employ high frequencies i.e. frequencies in the ultra violet, when measuring specimens. However, when using a polarimeter it is essential to know the precise wavelength of the light source and it is conventional to use sodium yellow, mercury green, and helium-neon wavelengths because these represent standard precisely known frequencies by means of which the polarimeter can be calibrated. An alternative method of calibrating a polarimeter exists which comprises using a standard sucrose solution. It is, however, a skilled operation to mix such a solution to an accurately known concentration. Furthermore such a solution does not form a fixed reference and is biologically unstable.

It is an object of the invention to provide a method by which a polarimeter can be calibrated to operate at desired relatively low frequencies, i.e. at frequencies in the near infra-red or at relatively high frequencies in the near ultra-violet. From another aspect it is an object of the invention to provide a polarimeter which can be accurately calibrated to work at such frequencies.

According to the invention a method of calibrating a polarimeter to work at a wavelength of unknown frequency comprises calibrating the polarimeter at a standard wavelength, using the calibrated polarimeter to measure a sample, measuring the same sample at the wavelength of unknown frequency and setting the polarimeter to give the same measurement at the said unknown wavelength as at the known wavelength.

From another aspect the invention is a polarimeter adapted to operate at a known wavelength of, for example, 589.44 nm and at another wavelength which may be in the near infra-red e.g. about 880 nm.

From another aspect the invention is a method of calibrating a saccharimeter to work at a wavelength of unknown frequency in the near infra-red, comprising calibrating the saccharimeter at a standard known wavelength, using the calibrated saccharimeter to measure a sugar sample, measuring the same sugar sample at the wavelength of unknown infra-red wavelength, and setting the saccharimeter to give the same measurement at the said unknown wavelength as at the known wavelength.

From a further aspect the invention is a polarimeter adapted to operate at a known wavelength and at another wavelength of unknown wavelength, wherein the polarimeter has an optical system comprising a light source, means for collimating light from the source, a pair of interference filters arranged such that they can be introduced alternately into the collimated light beam to produce two different wavelengths one of which passes light on a known wavelength and the other of which passes light at unknown wavelength, a polariser for polarising the light beam, means for introducing a sample to be tested into the polarised light beam, an analyser for receiving light transmitted through the sample and a light detection system, electrical means operatively connected to the analyser and detector for producing an output representative of the optical activity of the sample and calibration means for adjusting the output whereby the same output can be achieved when measuring the sample using the two different wavelengths. The light detection system is preferably constructed as described in our above-mentioned prior patents Nos. GB-B-1570067 and GB-B-1570068. It will be appreciated that the light source could be a quartz iodide lamp or indeed that two light sources could be employed. The light source may comprise a light emitting diode.

Preferably the polarimeter is controlled by means of a microprocessor accessed via a keyboard, with data being stored in a random access memory and/or electrically eraseable programmable memory ($E^2PROM$).

The pair of interference filters may be mounted on a rotatable turret.

From yet another aspect the invention is a saccharimeter adapted to operate at a known wavelength and at another wavelength of unknown wavelength in the near infra-red, wherein the polarimeter has an optical system comprising a light source, means for collimating light from the source, a pair of interference filters arranged such that they can be introduced alternately into the collimated light beam to produce two different wavelengths one of which passes light on a known wavelength and the other of which passes light at unknown wavelength in the near infrared, a polariser for polarising the light beam, means for introducing a sample to be tested into the polarised light beam, an analyser for receiving light transmitted through the sample and a light detection system, electrical measurement means operatively connected to the analyser and detector for producing a output representative of the optical activity of the sample and calibration means for adjusting the measurement means whereby the same output can be achieved when measuring the sample using the two different wavelengths.

BRIEF DESCRIPTION OF THE DRAWINGS

The invention is diagrammatically illustrated by way of example in the accompanying drawing which is a schematic block diagram of a saccharimeter embodying the invention.

DESCRIPTION OF THE PREFERRED EMBODIMENTS

Referring to the drawing, a saccharimeter embodying the invention is in the form of a polariser generally as described in our patent specifications Nos. GB1570067 and GB1570068. The saccharimeter includes a light source 1 constituted by a quartz iodide lamp and collimator 2. Collimated light 16 from the collimator 2 passes in turn through one of a pair of narrow band precision interference filters 3a and 3b, one of which is adapted to pass light at known wavelength e.g. that of sodium yellow, mercury green or helium-neon and the other of which is adapted to pass light at unknown (longer) wavelength in the near infra-red, e.g. around 880 nm. The pair of filters 3a and 3b are mounted on a rotatable turret (not shown) so that they can be brought alternately into the light path 16. The filtered light then passes through a polariser 4 having a fixed optical orientation and an analyser 6 which is rotatable about its axis. A light detector 8 which may be in the form of a photovoltaic silicon diode operated in the current mode, detects the intensity of the light transmitted by the analyser and delivers an electrical output signal proportional to the detected light intensity. A sugar sample 5, the optical activity of which is to be measured, can be introduced into the light path between the polariser 4 and the analyser 6.

In use, the analyser 6 is rotated at constant speed. so that the output electrical signal of the detector 8 has a $Sin^2$ waveform of two cycles per revolution of the analyser. When an optically active sugar sample 5 is introduced between the polariser and analyser, the phase of the $Sin^2$ waveform is shifted relative to the angular position of the analyser by an amount which is proportional to the optical rotation produced by the sample 5. This shift in phase is measured by the saccharimeter to determine the optical activity of the sample. To this end, the analyser 6 is rigidly connected to the rotor of a stepper motor 7 which is driven in synchronism with digital clock pulses delivered by a motor drive reference clock 9 so that each step of the motor corresponds to a predetermined number of clock pulses. This light detection system is fully described in the specifications of our patents GB-B-1570067 and GB-B-1570068.

In use of the saccharimeter, e.g. when it is desired to measure a dark sugar sample, the device is first calibrated by measuring a more or less standard sugar sample using light of known wavelength (i.e. by using the appropriate one of the filters 3) and the output reading or measurement of the saccharimeter is noted. The same sample is then measured using the other filter 3, i.e. that producing light of unknown near infra-red wavelength, and the device is adjusted so that output reading or measurement of the saccharimeter is the same when using this unknown infra-red wavelength as it was when using the standard filter. With the device thus calibrated, a dark sugar sample can then be measured using the filter producing light of unknown infra-red wavelength to penetrate the sample. This adjustment or calibration can conveniently be made by the user by control means in the form of a microprocessor and memory 12 accessed via a user keyboard 13 and which provides a display 14 and outputs 15.

The invention thus provides a simple and inexpensive method of calibrating a saccharimeter to operate at unknown light wavelengths whereby dark sugar samples can be measured.

We claim:

1. A method of calibrating a polarimeter to work at an unknown wavelength of comprising calibrating the polarimeter at a standard known wavelength, using the calibrated polarimeter to measure a sample, measuring the same sample at the unknown wavelength and setting the polarimeter to give the same measurement at the said unknown wavelength as at the known wavelength.

2. A method according to claim 1, wherein the unknown wavelength lies in the near infra-red at around 880 nm.

3. A method of calibrating a saccharimeter to work at an unknown wavelength in the near infra-red, comprising calibrating the saccharimeter at a standard known wavelength, using the calibrated saccharimeter to measure a sugar sample, measuring the same sugar sample at the unknown wavelength, and setting the saccharimeter to give the same measurement at the said unknown wavelength as at the known wavelength.

4. A polarimeter adapted to operate at a known wavelength and at another, unknown wavelength, wherein the polarimeter has an optical system comprising a light source, means for collimating light from the source, a pair of interference filters arranged such that they can be introduced alternately into the collimated light beam to produce two different wavelengths, one of which passes light at a known wavelength and the other of which passes light at an unknown wavelength, a polariser for polarising the light beam, means for introducing a sample to be tested into the polarised light beam, an analyser for receiving light transmitted through the sample and a light detection system, electrical means operatively connected to the analyser and detection system for producing an output representative of the optical activity of the sample and calibration means for adjusting the output whereby the same output can be achieved when measuring the sample using the two different wavelengths.

5. A polarimeter according to claim 4, comprising control means having a microprocessor accessed via a keyboard, and a random access memory in which data is stored.

6. A polarimeter according to claim 4, wherein the pair of interference filters are mounted on a rotatable turret.

7. A saccharimeter adapted to operate at a known wavelength and at another unknown, wavelength in the near infra-red, wherein said saccharimeter has an optical system comprising a light source, means for collimating light from the source, a pair of interference filters arranged such that they can be introduced alternately into the collimated light beam to produce two different wavelengths, one of which passes light at a known wavelength and the other of which passes light at an unknown wavelength in the near infra-red, a polariser for polarising the light beam, means for introducing a sample to be tested into the polarised light beam, an analyser for receiving light transmitted through the sample and a light detection system, electrical measurement means operatively connected to the analyser and detection system for producing output representative of the optical activity of the sample and calibration means for adjusting the measurement means whereby the same output can be achieved when measuring the sample using the two different wavelengths.

* * * * *